US010328018B2

United States Patent
Pegeon et al.

(10) Patent No.: US 10,328,018 B2
(45) Date of Patent: *Jun. 25, 2019

(54) **COSMETIC USE OF THE ESSENTIAL OIL OF *LASERPITIUM SILER* L. AGAINST THE SIGNS OF AGING OF THE SKIN AND AS A SKIN ANTIOXIDANT**

(71) Applicant: L'OREAL, Paris (FR)

(72) Inventors: Agnes Pegeon, Meudon (FR); Pascale Pelletier, Antony (FR); Pierre Lartaud, Eurre (FR); Corinne Ferraris, Crest (FR)

(73) Assignee: L'OREAL, Paris (FR)

(*) Notice: Subject to any disclaimer, the term of this patent is extended or adjusted under 35 U.S.C. 154(b) by 33 days.

This patent is subject to a terminal disclaimer.

(21) Appl. No.: 14/422,480

(22) PCT Filed: Aug. 20, 2013

(86) PCT No.: PCT/IB2013/056750
§ 371 (c)(1),
(2) Date: Feb. 19, 2015

(87) PCT Pub. No.: WO2014/030117
PCT Pub. Date: Feb. 27, 2014

(65) Prior Publication Data
US 2015/0231057 A1    Aug. 20, 2015

Related U.S. Application Data

(60) Provisional application No. 61/714,991, filed on Oct. 17, 2012, provisional application No. 61/714,953, filed on Oct. 17, 2012.

(30) Foreign Application Priority Data

Aug. 20, 2012 (FR) .................................. 12 57885
Aug. 20, 2012 (FR) .................................. 12 57886

(51) Int. Cl.
| | | |
|---|---|---|
| *A61K 36/23* | (2006.01) | |
| *A61K 8/92* | (2006.01) | |
| *A61Q 19/02* | (2006.01) | |
| *A61Q 19/08* | (2006.01) | |
| *A61Q 5/00* | (2006.01) | |
| *A61K 8/9789* | (2017.01) | |
| *A61Q 19/00* | (2006.01) | |

(52) U.S. Cl.
CPC ............ *A61K 8/922* (2013.01); *A61K 8/9789* (2017.08); *A61K 36/23* (2013.01); *A61Q 5/006* (2013.01); *A61Q 19/00* (2013.01); *A61Q 19/02* (2013.01); *A61Q 19/08* (2013.01); *A61K 2800/522* (2013.01)

(58) Field of Classification Search
None
See application file for complete search history.

(56) References Cited

U.S. PATENT DOCUMENTS

2004/0161436 A1    8/2004    Hull

FOREIGN PATENT DOCUMENTS

| DE | 19915102 A1 * | 10/2000 | ........... A61K 31/015 |
|---|---|---|---|
| FR | 2959666 A1 | 11/2011 | |
| FR | 2962328 A1 | 1/2012 | |
| JP | 2002 506800 A | 3/2002 | |
| WO | WO-99/47110 | 9/1999 | |
| WO | WO-2008/072941 A1 | 6/2008 | |
| WO | WO-2009/010021 A1 | 1/2009 | |
| WO | WO 2011101239 A2 * | 8/2011 | ............... A61K 8/25 |
| WO | WO-2012/080992 A2 | 6/2012 | |

OTHER PUBLICATIONS

Tirillini et al. (2009) Chemistry of Natural Compounds, vol. 45, No. 1, 103-105.*
Chizzola et al. (1999) J. Essential OI. Res., vol. 11, Issue 2, 197-198.*
Bickers et al. (2006) JCI, 126, 2565-2575.*
Bousbia et al. (2008) Food Chemistry 114, 355-362.*
Kapetanos et al. (2008) Chemistry and Biodiversity, vol. 5, 101-119.*
Okoh et al. (2010) Food Chemistry, 120: 308-312.*
Ruberto et al. (2000) Food Chemistry, 69: 167-174.*
Lechner et al., "Antimycobacterial Activity of *Laserpitium Siler* L. Roots", Supplement 1, Sci. Pharm. 74 (2006).
Bo Jensen, "Laserwort-Laserpitium Siler (Umbelliferae/Apiaceae)", Internet Citation, Apr. 26, 2012, pp. 1-2, XP002697255; retrieved from the Internet: URL:http://wayback.archieve.org/web/20120426092119/http://bojensen.net/EssentialOilsEng/EssentialOils15/EssentialOils15.htm [retrieved on May 14, 2013] the whole document.
Ruberto et al., "Antioxidant activity of selected essentail oil components in two lipid model systems", Food Chemistry 69 (2000) 167-174.
New Handbook for Cosmetics (in Japanese), Oct. 30, 2006, p. 518-524.

* cited by examiner

*Primary Examiner* — Christopher R Tate
*Assistant Examiner* — Russell G Fiebig
(74) *Attorney, Agent, or Firm* — Polsinelli PC

(57) ABSTRACT

The present invention relates to the cosmetic use of the essential oil of *Laserpitium siler* L., as an active agent for preventing and/or treating the signs of aging or photoaging of the skin and as an antioxidant. It also targets a method for cosmetic treatment of the skin in order to combat the signs of skin aging or photoaging and/or to prevent and/or treat skin disorders induced by an oxidative stress and also a composition comprising an essential oil of *Laserpitium siler* L.

7 Claims, No Drawings

COSMETIC USE OF THE ESSENTIAL OIL OF *LASERPITIUM SILER* L. AGAINST THE SIGNS OF AGING OF THE SKIN AND AS A SKIN ANTIOXIDANT

CROSS REFERENCE TO RELATED APPLICATIONS

This application is a National Phase filing under 35 U.S.C. § 371 of PCT/IB2013/056750 filed on Aug. 20, 2013; and this application claims priority to Application No. 1257885 filed in France on Aug. 20, 2012 and Application No. 1257886 filed in France on Aug. 20, 2012; and this application claims the benefit of U.S. Provisional Application No. 61/714,991 filed on Oct. 17, 2012 and U.S. Provisional Application No. 61/714,953 filed on Oct. 17, 2012. The entire contents of each application are hereby incorporated by reference.

The present invention relates to the field of cosmetic and/or dermatological products.

More particularly, the present invention aims to provide a novel active agent for treating the signs of skin aging or photoaging and/or that is used as an antioxidant.

Human skin is constituted of three compartments, namely a superficial compartment, which is the epidermis, the dermis and a deep compartment, which is the hypodermis.

The dermis provides the epidermis with a solid support. It is also its nourishing element. It is mainly constituted of fibroblasts and an extracellular matrix (ECM).

This extracellular matrix is constituted of various macromolecules responsible for the mechanical strength of the skin, its suppleness, its tonicity and its elasticity, and also for physiologically important functions (hydration, thermoregulation and regulation of the permeability of the skin). These macromolecules include, in particular, collagens, elastin and glycoconjugates (glycoproteins and proteoglycans).

Collagens represent 70% of the proteins of the ECM. In the skin, many types of collagen constitute the ECM, including in particular interstitial collagens (of type I, II, III) of fibrillar structure, produced essentially by the fibroblasts, and responsible for the cohesion, rigidity and mechanical strength, collagens of the basal laminae (of type IV) synthesized by the adjacent cells and in the skin by keratinocytes and that play in particular a mechanical role, and collagens that form anchoring fibrils of the basement membrane (dermo-epidermal junction) expressed by the epidermal keratinocytes (of type VII).

It is also known that the synthesis of collagen starts with the assembly of procollagen units. For example, for the synthesis of type I collagen, these are type I procollagen units (also referred to as Pro-Coll1).

Naturally, the collagen fibers are constantly renewed, but this renewal decreases with age, which leads to thinning of the dermis. Similarly, it is also accepted that extrinsic factors such as ultraviolet radiation, tobacco or certain treatments (glucocorticoids, vitamin D and derivatives, for example) also have an effect on the skin and its collagen content.

Thus, prolonged exposure to ultraviolet radiation, particularly to type A and B radiation, has the effect of stimulating the expression of collagenases, particularly of MMPI (also referred to as matrix metalloproteinase 1 or else interstitial collagenase), constituting one of the components of photoinduced or non-photoinduced skin aging.

A set number of active agents are already proposed for preventing and/or treating the signs of skin aging.

It is thus known to use hydroxystilbene compounds in order to stimulate the synthesis of collagen and/or the proliferation of dermal fibroblasts, as described in French application FR 2 777 186.

The use of the combination of a metalloproteinase inhibitor with a myorelaxant or relaxant described in French application FR 2 859 908 and the use of a berry extract, and more particularly a wolfberry extract, described in French application FR 2 930 154 for preventing and/or treating the signs of skin aging are also known.

Finally, vitamins, for example vitamin C, hormones, for example DHEA (dehydroepiandrosterone) or else growth factors such as TGF-β1 (Transforming Growth Factor-β1) have also been benefited from for this purpose.

Furthermore, as mentioned previously, skin aging may be photoinduced, i.e. it may be caused following exposure to the sun. This aging is then referred to as photoaging or dermatoheliosis.

This results in a peroxidation of the lipids of surfaces of the skin and/or scalp and in particular the photoinduced peroxidation of the lipids of sebaceous origin, such as squalene. Indeed, it is known that the lipids that are found at the surface of the skin, scalp and hair are permanently subjected to external attacking factors and in particular the air, atmospheric pollutants and visible radiation and especially ultraviolet (UV) radiation and that the ones that are most exposed to external attacking factors are those contained in the oily secretions of the skin such as sebum, which is rich in squalene. The presence, in the squalene molecules, of six double bonds makes these molecules sensitive to oxidation phenomena. Thus, during prolonged exposure to UV radiation, squalene is photoperoxidized to give squalene peroxides. This high production of squalene peroxides causes in particular a series of chain degradations, in particular in and on the skin, giving rise to many skin disorders, including photoaging.

Many agents or treatments for preventing and/or treating photoaging already exist such as vitamin A, botulinum toxin, dermal fillers, various laser treatments, dermabrasion and peels.

Furthermore, the use of antioxidants in cosmetics is very high and increasingly widespread. Thus, antioxidants make it possible to combat the free radicals ($O^-_2$, $OH°$, $^1O_2$, etc.) that induce more generally cell aging.

They can thus be used in various cosmetic lines such as those for anti-aging, protection against oxidative stress and especially exogenous stress due to exposure to the sun, to the environment (pollution, smoke), and to the action of microbial agents, anti-pigmentation (the synthesis of melanin is an oxidative process), or else oily skin and oily scalp (preservation of the quality of the sebum).

This antioxidant activity is in particular advantageous for limiting the peroxidation of the lipids of surfaces of the skin and/or scalp and in particular the photoinduced peroxidation of the lipids of sebaceous origin, such as squalene, whose consequences were mentioned above.

Many antioxidants exist already, such as tocopherol (vitamin E) or derivatives thereof, vitamin C or derivatives thereof, carotenoids, ubiquinone, green tea, etc.

FR 2 962 328 describes a cosmetic method for treating the body odors linked to human perspiration comprising the application to the keratin materials of a composition comprising at least one 2-alkoxy-4-alkylketonephenol compound and at least one essential oil.

FR 2 959 666 describes a cosmetic composition comprising ellagic acid, or a derivative thereof, and at least one essential oil having anti-dandruff properties.

WO 2012/080992 describes the cosmetic use of at least one extract of at least one plant of the species *Bupleurum fruticosum* L. for treating and/or preventing the signs of skin aging.

US 2004/161436 describes a topical composition comprising d-limonene in order to treat acne, the effects on the skin linked to age, in order to smooth out fine lines, wrinkles and cellulite, and in order to treat red patches, spots, enlarged pores and ecchymoses.

Lechner et al. ("Antimycobacterial activity of *Laserpitium Siler* L. Roots", April 2006, Sci. Pharm. 74, Suppl. 1) describes the anti-mycobacterial activity of the roots of Laser siler.

Bo Jensen ("Laserwort—*Laserpitium siler* (Umbelliferae/ Apiaceae)", http://www.bojensen.net/EssentialOilsEng/EssentialOils15/EssentialOils15.htm#*Laserpitium* dated 26 Apr. 2012) states that the essential oil of *Laserpitium siler* comprises 89.5% of perillaldehyde and 10.5% of limonene.

WO 2009/010021 describes the use of the trilobolide obtained from roots of *Laserpitium siler* in order to stimulate the immune system.

WO 2008/072941 describes an antioxidant composition that has a protective activity with respect to the skin, in particular having an anti-dandruff, anti-acne and anti-aging effect, and comprising glycyrrhizin, quercetin, rosmarinic acid, madecassic acid, chamazulene, biacalein and emodin.

Ruberto et al. (Food Chemistry, vol 69, no 2, "Antioxidant activity of selected essential oil components in two lipid model systems") describes the antioxidant properties of limonene and perillaldehyde.

However, there remains a permanent need to provide novel active agents capable of exerting a beneficial cosmetic action on the signs of skin aging, in particular chronological aging, or photoaging and/or that are capable of exerting an antioxidant cosmetic action and in particular of combating oxidative stress of the skin and/or hair and/or limiting the oxidation of cosmetic products/formulas and therefore their deterioration over time.

The object of the present invention is to satisfy these needs.

Thus, according to a first subject matter, the present invention relates to the cosmetic use of the essential oil of *Laserpitium siler* L., as an active agent for preventing and/or treating the signs of aging, in particular chronological aging, or photoaging of the skin and/or as an antioxidant.

Quite unexpectedly, the inventors have indeed demonstrated that the essential oil of *Laserpitium siler* L. has an anti-aging and/or antioxidant activity.

One of the advantages of the essential oil of *Laserpitium siler* L. according to the invention is to provide a natural active agent.

In particular, according to this first aspect, the present invention aims to protect the cosmetic use of the essential oil of *Laserpitium siler* L. for preventing and/or treating aged or senescent skins, in particular for preventing and/or treating wrinkles and/or fine lines and/or cracks, thinning of the skin, in particular of the dermis, and/or senescence spots.

Also according to this first aspect, the present invention relates to the prevention and/or treatment of wrinkles and/or fine lines and/or cracks, thinning of the skin, in particular of the dermis, and/or senescence spots.

The expression "treatment of wrinkles and/or fine lines" is understood according to the present invention to mean the fact of softening wrinkles and/or fine lines, or of reducing the appearance of wrinkles and/or fine lines.

Moreover, the essential oil of *Laserpitium siler* L. according to the invention makes it possible to combat the loss of firmness and/or of elasticity and/or of tonicity and/or of suppleness and/or the slackening of the skin.

Equally, the present invention aims to protect the cosmetic use of the essential oil of *Laserpitium siler* L. for combating skin disorders induced by an oxidative stress chosen from a dull appearance of the complexion, and/or hyperpigmentation of the skin, and/or a loss of quality of the sebum, and/or a dandruff appearance of the scalp, and/or a feeling of discomfort on the scalp.

This oxidative stress may especially originate from exposure to the sun or maybe due to the environment, such as pollution or smoke.

The protection of the quality of the sebum is beneficial both for the skin, especially for the face, and for the scalp. Indeed, UV radiation degrades the lipids of the sebum and generates pro-inflammatory fatty acids which, in the case of the scalp, may give rise to a feeling of discomfort and may promote dandruff.

Another advantage of the present invention is that generally, in the cosmetic products intended to reduce pigmentation, it is necessary to combine an antioxidant, an anti-inflammatory and a desquamating agent for the "anti-darkening". Thus, the cosmetic use of the essential oil of *Laserpitium siler* L. in such cosmetic products makes it possible to avoid adding a supplementary antioxidant.

Still according to this first aspect, the present invention relates to the cosmetic use of the essential oil of *Laserpitium siler* L. to stimulate the expression of procollagen I and/or to inhibit the expression of the type I metalloproteinase of the extracellular matrix.

The inhibitory activity of MMP-1 (without UV radiation) makes it possible to prevent the degradation of the collagen fibers due to skin aging and thus to maintain the quality of the dermis.

As regards the stimulating activity on the synthesis of pro-Coll1, it makes it possible to obtain these same effects.

The essential oil of *Laserpitium siler* L. is not, to date, known for being used against the signs of skin aging or photoaging.

The present invention also aims to protect a method for cosmetic treatment of the skin in order to combat the signs of skin aging, in particular chronological aging, or photoaging and/or to prevent and/or treat skin disorders induced by an oxidative stress, comprising at least one step that consists in applying, to the skin or to the scalp, in particular exhibiting such signs of skin aging or photoaging or skin disorders induced by an oxidative stress, at least one composition comprising the essential oil of *Laserpitium siler* L.

The present invention also aims to protect a method for cosmetic treatment of the skin in order to combat the signs of skin aging, in particular chronological aging, or photoaging comprising at least one step that consists in applying to the skin exhibiting such signs of skin aging or photoaging, at least one composition comprising the essential oil of *Laserpitium siler* L.

The present invention also aims to protect a cosmetic treatment method in order to prevent and/or treat skin disorders induced by an oxidative stress, comprising at least one step that consists in applying, to skin or the scalp, in particular exhibiting skin disorders induced by an oxidative stress, at least one composition comprising the essential oil of *Laserpitium siler* L.

The extent of the damage generated by this oxidative stress depends on the rapidity with which the free radicals are created and subsequently deactivated by antioxidants.

The terms "preventing" or "prevention" are understood according to the invention to mean the fact of reducing the risk of the occurrence or of slowing down the occurrence of a given phenomenon, namely, according to the present invention, in particular skin disorders induced by an oxidative stress such as a dull appearance of the complexion, and/or hyperpigmentation of the skin, and/or a loss of quality of the sebum, and/or a dandruff appearance of the scalp, and/or a feeling of discomfort on the scalp, or else the signs of aging or photoaging of the skin, aged or senescent skins, wrinkles and/or fine lines and/or cracks, thinning of the skin, in particular of the dermis, and/or senescence spots.

A composition that is suitable for the invention, namely intended for the implementation of the invention, may be a cosmetic or dermatological composition depending on the envisaged application, and therefore comprises a physiologically acceptable medium.

Thus, according to one preferred embodiment, the essential oil of *Laserpitium Siler* L. is contained in a cosmetic composition comprising a physiologically acceptable medium.

The essential oil of *Laserpitium Siler* L. according to the invention may also be useful in order to limit the oxidation of the cosmetic compositions and therefore their deterioration over time.

The term "physiologically acceptable medium" means a medium that is compatible with all keratin materials such as the skin, the scalp, the nails, the mucous membranes, the eyes and the hair, or any other area of bodily skin. A physiologically acceptable medium is preferentially a cosmetically or dermatologically acceptable medium, i.e. a medium that has no unpleasant odor, color or appearance, and that is entirely compatible with the route of administration under consideration.

Essential Oil of *Laserpitium siler* L.

A composition that is suitable for the invention comprises the essential oil of *Laserpitium siler* L.

*Laserpitium siler* L., also referred to as Laser siler, laserwort or *siler montanum*, is a plant belonging to the Apiaceae family. It is a perennial plant measuring from 40 to 130 cm in height, which has an imposing umbel in the flowering period (July-August).

This plant is found on rocky ground and dry prairies of the semi-mountainous regions of southern Europe at an altitude between 400 m and 2000 m.

This plant can more particularly be found in France, in particular in the Jura, the Alps, the Cévennes, the Corbières and the Pyrenees and more particularly in the Vercors, the Gapençais region and the Briançonnais zone.

According to the definition given in international standard ISO 9235 and adopted by the Commission of the European Pharmacopoeia, an essential oil is an odorous product generally of complex composition, obtained from a botanically defined plant raw material, either by steam distillation, or by dry distillation, or via an appropriate mechanical method without heating (cold pressing). The essential oil is generally separated from the aqueous phase by a physical method which does not result in any significant change in the composition.

Modes for Obtaining Essential Oils

The choice of technique depends mainly on the raw material: its original state and its characteristics, its actual nature. The "essential oil/plant raw material" yield may be extremely variable depending on the plants: 15 ppm to more than 20%. This choice determines the characteristics of the essential oil, in particular viscosity, color, solubility, volatility, and richness or poorness in certain constituents.

Mention may be made, among the methods for obtaining an essential oil, of steam distillation and dry distillation.

Steam distillation corresponds to the vaporization, in the presence of steam, of a substance which is not very miscible with water. The raw material is placed in contact with boiling water or steam in an alembic. The steam entrains the essential oil vapor, which is condensed in the condenser in order to be recovered as liquid phase in a Florentine flask (or essence jar), where the essential oil is separated from the water by settling. The term "aromatic water" or "hydrolat" or "distilled floral water" is used to describe the aqueous distillate which remains after the steam distillation, once the essential oil has been separated.

Dry distillation consists in obtaining the essential oil by distillation of woods, barks or roots, without addition of water or steam, in a closed chamber designed so that the liquid is recovered at the bottom. Cade oil is the best known example of a product obtained in this way.

Preferably, an essential oil of *Laserpitium siler* L. according to the invention is prepared by the steam distillation method.

Physicochemical Characteristics

Essential oils are generally volatile and liquid at room temperature, which distinguishes them from "set" oils. They are more or less colored and their density is generally less than that of water. They have a high refractive index and most of them deflect polarized light. They are liposoluble and soluble in the usual organic solvents, steam distillable, and very sparingly soluble in water.

Plant Raw Materials

An essential oil of *Laserpitium siler* L. according to the invention can be prepared from any plant material derived from at least one *Laserpitium siler* L. cultivated in vivo or derived from in vitro cultivation.

The term "in vivo cultivation" is understood to mean any cultivation of standard type, i.e. in soil in the open air or in a greenhouse, or else out of the soil.

The term "in vitro cultivation" is understood to mean all the techniques known to a person skilled in the art for artificially obtaining a plant or a plant part. The selection pressure imposed by the physicochemical conditions during the growth of plant cells in vitro makes it possible to obtain a standardized plant material which is available throughout the year, in contrast to plants cultivated in vivo.

The essential oil of *Laserpitium siler* L. used in the present invention may be obtained from any plant material derived from this whole plant or from any part of this plant, for instance the leaves, stems, roots, flowers, petals, seeds, umbels, fruits and buds, which are in various states of dryness (dry, withered or fresh form).

Preferably, an essential oil of *Laserpitium siler* L. according to the invention is obtained from leaves and/or umbels and/or seed-bearing umbels and/or seeds of the fruits of *Laserpitium siler* L., more preferably from leaves and/or umbels, and more preferably still from seed-bearing umbels.

According to a preferred embodiment, an essential oil of *Laserpitium siler* L. according to the invention is obtained from umbels and/or seed-bearing umbels, and more preferably from seed-bearing umbels.

According to a preferred embodiment, an essential oil of *Laserpitium siler* L. according to the invention is obtained from leaves.

Advantageously, the umbels or the seeds may be pre-dried and ground.

An essential oil in accordance with the invention may be prepared according to the techniques mentioned above.

As specified above, preferably, an essential oil in accordance with the invention is obtained according to the standard technique of steam distillation.

Advantageously, an essential oil according to the invention is obtained from umbels of the fruits of *Laserpitium siler* L., by hydrodistillation or steam distillation through a glass apparatus, a still (4-liter Clevenger type apparatus), as defined in the European Pharmacopoeia for determining the essential oil of a plant material.

Preferably, the essential oil according to the invention is prepared from the seed-bearing umbels of *Laserpitium siler* L. by hydrodistillation.

According to the present invention, the essential oil of *Laserpitium siler* L. will be able to be used in a sufficient amount in order to obtain the desired effect, i.e. in a sufficient amount to treat the signs of aging, in particular chronological aging, or photoaging of the skin.

Preferably, the essential oil of *Laserpitium siler* L. is used at a content ranging from 0.0001% to 10% by weight, preferably from 0.001% to 1% by weight and very preferably from 0.01% to 0.5% by weight, relative to the total weight of the cosmetic composition.

Preferably, the essential oil of *Laserpitium siler* L. is used in a dermatological composition, in particular at a content ranging from 0.0001% to 10% by weight, preferably from 0.001% to 1% by weight, relative to the total weight of the dermatological composition.

The chemical composition of the essential oil of *Laserpitium siler* L. in accordance with the invention thus obtained can be analyzed by conventional techniques known to a person skilled in the art, such as gas chromatography GC analysis, chromatographic analysis with flame ionization detection, referred to as GC-FID, or GC/MS analysis, which consists of the use of a mass spectrometer coupled to a gas chromatograph.

Advantageously, the essential oil of *Laserpitium siler* L. predominantly contains limonene, perillaldehyde and chamazulene. These three compounds are well known.

Limonene, of empirical formula $C_{10}H_{16}$, is a chiral terpene hydrocarbon. At ambient temperature, it is a colorless liquid with a fresh odor specific to orange, characteristic of citrus fruits. Limonene may be present in the essential oil of *Laserpitium siler* L. at a content ranging from 40% to 80% by weight, preferably ranging from 50% to 70% by weight, relative to the total weight of said essential oil.

Perillaldehyde or *perilla* aldehyde, of empirical formula $C_{10}H_{14}O$, is a monoterpene comprising an aldehyde function. Perillaldehyde may be present in the essential oil of *Laserpitium siler* L. at a content ranging from 15% to 40% by weight, preferably ranging from 20% to 35% by weight, relative to the total weight of said essential oil.

Chamazulene is a sesquiterpene hydrocarbon of blue color. Chamazulene may be present in the essential oil of *Laserpitium siler* L. at a content of less than or equal to 5%, preferably of less than or equal to 2% by weight, relative to the total weight of said essential oil.

An essential oil in accordance with the invention may be used as is, i.e. alone, or may be introduced into a composition, in particular a cosmetic or dermatological composition.

Advantageously, an essential oil of *Laserpitium siler* L. in accordance with the invention comprises an amount of limonene ranging from 40% to 80% by weight, preferably ranging from 50% to 70% by weight relative to the total weight of said essential oil, an amount of perillaldehyde ranging from 15% to 40% by weight, preferably ranging from 20% to 35% by weight relative to the total weight of said essential oil, and an amount of chamazulene of less than or equal to 5%, preferably of less than or equal to 2% by weight, relative to the total weight of said essential oil.

According to another embodiment, an essential oil of *Laserpitium siler* L. according to the invention is constituted of at least 40% by weight, preferably of at least 50% by weight, and better still of at least 65% by weight of monoterpenes chosen from limonene, myrcene, sabinene, gamma-terpinene, para-cymene and alpha-pinene.

Composition

Preferably, a composition that is suitable for the invention is intended for a cosmetic application.

It can in particular be administered topically or orally.

As indicated previously, an essential oil of *Laserpitium siler* L. according to the present invention predominantly contains limonene, perillaldehyde and chamazulene.

Thus, according to one particular embodiment, a cosmetic composition suitable for the invention comprises an essential oil of *Laserpitium siler* L. in accordance with the invention comprising an amount of limonene ranging from 40% to 80% by weight, preferably ranging from 50% to 70% by weight relative to the total weight of said essential oil, an amount of perillaldehyde ranging from 15% to 40% by weight, preferably ranging from 20% to 35% by weight relative to the total weight of said essential oil, and an amount of chamazulene of less than or equal to 5%, preferably of less than or equal to 2% by weight, relative to the total weight of said essential oil.

Preferably, a composition according to the invention is devoid of ellagic acid and/or ellagic acid derivatives, in particular those described in FR 2 959 666.

Preferably, alternatively or in addition, a composition according to the invention is devoid of a compound of 2-alkoxy-4-alkylketonephenol type, and in particular of vanillylacetone, in particular those described in FR 2 962 328.

Preferably, an essential oil according to the invention, when it is present in a composition, may be formulated in a physiologically acceptable medium.

When the composition is intended to be administered topically, such a medium is considered as being physiologically acceptable when it does not cause any stinging, tautness or redness that is unacceptable to the user.

Advantageously, a composition that is suitable for the invention comprising an essential oil of *Laserpitium siler* in accordance with the invention is intended for topical administration.

A composition that is suitable for the invention can be provided in any galenic form normally used in the cosmetic and dermatological fields.

It may especially be in the form of an aqueous or aqueous-alcoholic solution, which is optionally gelled, an optionally two-phase lotion-type dispersion, an oil-in-water or water-in-oil or multiple emulsion, an aqueous gel, a gelled or non-gelled oil, a dispersion of oils in an aqueous phase, especially with the aid of spherules, these spherules possibly being polymer particles or, better still, lipid vesicles of ionic and/or nonionic type, or alternatively in the form of a powder, a serum, a paste or a flexible stick. It can have a solid, pasty or more or less fluid liquid consistency.

For example, these compositions may be makeup or care products for keratin materials, in particular for the skin. More specifically, the makeup products may be of the foundation, face powder or eyeshadow, concealer or blusher type, or else a makeup product for the body or for coloring the skin.

The skincare products may be a protective, treatment or care composition for the face, for the hands, for the feet, for the major anatomical folds or for the body (for example day creams, night creams, makeup-removing cream, anti-sun composition, protective or care body milks, after-sun milks, skincare lotion, gel or foam, or artificial tanning composition), or an aftershave composition.

Thus, the composition may comprise all the constituents customarily used in the topical application and administration envisaged. Mention may especially be made of water, solvents, oils of mineral, animal and/or plant origin, especially as described in detail below, waxes, especially as described below, pigments, fillers, surfactants, thickeners, gelling agents, preservatives, and mixtures thereof.

A composition that is suitable for the invention may also contain various adjuvants commonly used in the cosmetics field, such as sequestrants, odor absorbers, UV screening agents, fragrances, matting agents, fluorescent agents, soft-focus fillers, and abrasive fillers or exfoliants, and mixtures thereof.

A composition that is suitable for the invention may advantageously comprise at least one additional active agent or supplementary compound.

In the context of the present invention, the expression "additional active agent" is understood to mean a compound which has on its own, i.e. not requiring the intervention of an external agent to activate it, a biological activity. Such an additional active agent or supplementary compound may be in particular:
- a metalloproteinase (MMP) inhibitor, and/or
- a photoprotective agent and/or
- a moisturizer or humectant, and/or
- a myorelaxant or relaxant, and/or
- an agent that stimulates the synthesis of collagen, and/or
- an agent that stimulates the synthesis of elastin, and/or
- an agent that stimulates the synthesis of glycosaminoglycans,
- an agent that stimulates the synthesis of fibronectin, and/or
- an agent that stimulates fibroblast proliferation, and/or
- an agent that stimulates keratinocyte proliferation and/or differentiation, and/or
- a supplementary antioxidant, and/or
- a desquamating agent, and/or
- an agent that improves the barrier function, and/or
- a depigmenting agent, and/or
- an agent that promotes the maturation of the horny envelope, and/or
- an agent that promotes the microcirculation of the skin or scalp, and/or
- a calmative or anti-irritant, and/or
- an astringent, and/or
- an agent for combating hair loss, and/or
- an antidandruff agent.

Particularly preferably, the additional active agent is chosen from the supplementary antioxidants, agents for combating hair loss, antidandruff agents, desquamating agents, depigmenting agents, moisturizers, and mixtures thereof.

More particularly preferably still, the additional active agent is chosen from the supplementary antioxidants.

The additional active agent used in a composition that is suitable for the invention may represent from 0.0001% to 20%, preferably from 0.01% to 10% and better still from 0.01% to 5% by weight relative to the total weight of the composition.

Furthermore, a composition that is suitable for the invention may advantageously comprise from 5% to 80% by weight, and preferably from 35% to 75% by weight of water relative to the total weight of said composition.

The composition could also be essentially oily (massage oil).

A composition that is suitable for the invention may advantageously have a firm and compact feel when taken up. It may be thick on application and then become transformed, melt and release freshness.

Needless to say, a person skilled in the art will take care to select this or these optional additional compound(s), and/or the amount thereof, such that the advantageous properties of the essential oil according to the invention are not, or are not substantially, adversely affected by the envisaged addition, and such that the properties of the compositions resulting therefrom are compatible with the preferred route of administration.

A composition that is suitable for the invention may advantageously comprise at least one fatty phase that is liquid at room temperature and at atmospheric pressure.

As examples of oils that may be used in a composition that is suitable for the invention, mention may be made of:
- hydrocarbon-based oils of animal origin, such as perhydrosqualene;
- hydrocarbon-based oils of plant origin, such as liquid triglycerides of fatty acids containing from 4 to 10 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stearineries Dubois or those sold under the names Miglyol 810, 812 and 818 by the company Dynamit Nobel, jojoba oil and shea butter oil;
- synthetic esters and ethers, especially of fatty acids, for instance the oils of formulae $R_1COOR_2$ and $R_1OR_2$ in which $R_1$ represents a fatty acid residue containing from 8 to 29 carbon atoms and $R_2$ represents a branched or unbranched hydrocarbon-based chain containing from 3 to 30 carbon atoms, for instance Purcellin oil, isononyl isononanoate, isopropyl myristate, 2-ethylhexyl palmitate, 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate, triisocetyl citrate, and fatty alcohol heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;
- linear or branched hydrocarbons of mineral or synthetic origin, such as volatile or non-volatile liquid paraffins, and derivatives thereof, isohexadecane, isododecane, petroleum jelly, polydecenes, and hydrogenated polyisobutene such as Parleam® oil;
- supplementary natural or synthetic essential oils;
- fatty alcohols containing from 8 to 26 carbon atoms, for instance cetyl alcohol, stearyl alcohol and a mixture thereof (cetylstearyl alcohol), octyldodecanol, 2-butyloctanol, 2-hexyldecanol, 2-undecylpentadecanol, oleyl alcohol or linoleyl alcohol;
- partially hydrocarbon-based and/or silicone-based fluoro oils, for instance those described in document JP-A-2 295 912;
- silicone oils, for instance volatile or non-volatile polymethylsiloxanes (PDMSs) with a linear or cyclic silicone chain, which are liquid or pasty at room temperature, especially cyclopolydimethylsiloxanes (cyclomethicones) such as cyclohexasiloxane and cyclopentasiloxane; polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes or 2-phenylethyl trimethylsiloxy silicates, and polymethylphenylsiloxanes; and mixtures thereof.

In the list of the abovementioned oils, the term "hydrocarbon-based oil" is understood to mean any oil predominantly comprising carbon and hydrogen atoms, and optionally ester, ether, fluoro, carboxylic acid and/or alcohol groups.

The other fatty substances that may be present in the oily phase are, for example, waxes and fatty acids comprising from 8 to 30 carbon atoms, for instance stearic acid, lauric acid, palmitic acid and oleic acid.

As waxes that may be used according to the invention, mention may be made of waxes of animal origin such as beeswax, spermaceti, lanolin wax and lanolin derivatives, plant waxes such as carnauba wax, candelilla wax, ouricury wax, Japan wax, cocoa butter, cork fiber wax or sugarcane wax, mineral waxes, for example paraffin wax, petroleum jelly wax, lignite wax or microcrystalline waxes or ozokerites, synthetic waxes, among which are polyethylene waxes, polytetrafluoroethylene waxes and the waxes obtained by Fischer-Tropsch synthesis or alternatively silicone waxes, hydrogenated oils that are solid at 25° C., such as hydrogenated castor oil, hydrogenated jojoba oil, hydrogenated palm oil, hydrogenated tallow or hydrogenated coconut oil, and fatty esters that are solid at 25° C., for instance the $C_{20}$-$C_{40}$ alkyl stearate sold under the trade name Kester Wax K82H by the company Koster Keunen.

These fatty substances can be chosen in a varied manner by a person skilled in the art so as to prepare a composition having the desired properties, for example of consistency or texture.

The compositions that are suitable for the invention may comprise a volatile oil.

For the purposes of the invention, the term "volatile oil" means an oil that is capable of evaporating on contact with keratin materials in less than one hour, at room temperature and atmospheric pressure. The volatile organic solvent(s) and volatile oils of the invention are volatile organic solvents and cosmetic oils that are liquid at room temperature, with a non-zero vapor pressure at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg), and more particularly ranging from 1.3 Pa to 1300 Pa (0.01 to 10 mmHg).

Volatile oils that may be mentioned, inter alia, include linear or cyclic silicones containing from 2 to 6 silicon atoms, such as cyclohexasiloxane, dodecamethylpentasiloxane, decamethyltetrasiloxane, butyltrisiloxane and ethyltrisiloxane. It is also possible to use branched hydrocarbons, for instance isododecane, and also volatile perfluoroalkanes such as dodecafluoropentane and tetradecafluorohexane, sold under the names PF 5050® and PF 5060® by the company 3M, and perfluoromorpholine derivatives, such as 4-trifluoromethylperfluoromorpholine sold under the name PF 5052® by the company 3M.

The amount of oily phase present in the compositions that are suitable for the invention can range, for example, from 0.01% to 50% by weight and preferably from 0.1% to 30% by weight, relative to the total weight of the composition.

A composition that is suitable for the invention can advantageously be provided in the form of an emulsion, obtained in particular by dispersion of an aqueous phase in a fatty phase (W/O) or of a fatty phase in an aqueous phase (O/W), of liquid or semi-liquid consistency of the milk type, or of soft, semi-solid or solid consistency of the cream or gel type, or alternatively of a multiple emulsion (W/O/W or O/W/O). These compositions are prepared according to the usual methods.

A composition of this type may be in the form of a face and/or body care or makeup product, and may be packaged, for example, in the form of cream in a jar or of fluid in a tube or a pump-action bottle.

The emulsions that are suitable for the invention may comprise at least one emulsifier chosen from amphoteric, anionic, cationic and nonionic emulsifiers, used alone or as a mixture.

Advantageously, the emulsifiers are appropriately chosen according to the emulsion to be obtained (W/O or O/W). The emulsifiers are generally present in the composition in a proportion that may range from 0.3% to 30% by weight and preferably from 0.5% to 20% by weight, relative to the total weight, of the composition.

Examples of emulsifiers that may be mentioned for the O/W emulsions include nonionic surfactants, and especially esters of polyols and of fatty acids with a saturated or unsaturated chain containing, for example, from 8 to 24 carbon atoms and better still from 12 to 22 carbon atoms, and the oxyalkylenated derivatives thereof, i.e. derivatives containing oxyethylenated and/or oxypropylenated units, such as the glyceryl esters of $C_8$-$C_{24}$ fatty acids, and the oxyalkylenated derivatives thereof; polyethylene glycol esters of $C_8$-$C_{24}$ fatty acids, and the oxyalkylenated derivatives thereof; sorbitol esters of $C_8$-$C_{24}$ fatty acids, and the oxyalkylenated derivatives thereof; sugar (sucrose, glucose or alkylglucose) esters of $C_8$-$C_{24}$ fatty acids, and the oxyalkylenated derivatives thereof; fatty alcohol ethers; the sugar ethers of $C_8$-$C_{24}$ fatty alcohols, and mixtures thereof.

A composition that is suitable for the invention may also comprise at least one silicone elastomer, for instance the products sold under the KSG names by the company Shin-Etsu, under the Trefil, BY29 or EPSX names by the company Dow Corning, or under the Gransil names by the company Grant Industries.

A composition that is suitable for the invention may also comprise at least one colorant chosen, for example, from pigments, nacres, dyes, materials with an effect, and mixtures thereof.

These colorants may be present at a content ranging from 0.01% to 50% by weight and preferably from 0.01% to 30% by weight relative to the total weight of the composition.

A composition that is suitable for the invention can additionally comprise at least one filler, in particular at a content ranging from 0.01% to 50% by weight and preferably ranging from 0.01% to 30% by weight, relative to the total weight of the composition.

These fillers may be mineral or organic and of any shape, platelet-shaped, spherical or oblong, irrespective of the crystallographic form (for example lamellar, cubic, hexagonal, orthorhombic or amorphous).

Mention may be made of silica, talc, mica, kaolin, lauroyl lysine, starch, boron nitride, PTFE powders, PMMA powders, methylsilsesquioxane resin powders (for instance Tospearl 145A from GE Silicone), hollow silicone resin hemispherical particles (for instance NLK 500, NLK 506 and NLK 510 from Takemoto Oil and Fat), barium sulfate, precipitated calcium carbonate, magnesium carbonate, magnesium hydrogen carbonate, hydroxyapatite, glass or ceramic microcapsules, and metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate.

In the case of oral administration, the composition may be in the form of tablets, gel capsules, sugar coated tablets, syrups, suspensions, solutions, powders, granules, emulsions, or suspensions of microspheres, nanospheres or lipid or polymeric vesicles allowing controlled release. Preferably, the composition is in the form of a food supplement.

A composition that is suitable for the invention may be manufactured via any known method generally used in the cosmetic or dermatological fields.

The cosmetic treatment method of the invention is advantageously carried out by topically administrating a composition comprising an essential oil of *Laserpitium siler* L. in accordance with the invention.

The topical administration consists of the external application to the skin of cosmetic and/or dermatological compositions according to the customary technique for using these compositions.

According to one particular embodiment, the cosmetic treatment method according to the present invention is characterized in that said essential oil is obtained from leaves and/or umbels and/or seed-bearing umbels and/or seeds of the fruits of *Laserpitium siler* L., more preferably from leaves and/or umbels, and more preferably still from seed-bearing umbels.

According to one particular embodiment, the cosmetic treatment method according to the invention is characterized in that said essential oil is used at a content ranging from 0.0001% to 10% by weight, preferably from 0.001% to 1% by weight and very preferably from 0.01% to 0.5% by weight, relative to the total weight of the cosmetic composition.

According to another particular embodiment, said method is characterized in that said essential oil of *Laserpitium siler* L. comprises an amount of limonene ranging from 40% to 80% by weight, preferably ranging from 50% to 70% by weight relative to the total weight of said essential oil, an amount of perillaldehyde ranging from 15% to 40% by weight, preferably ranging from 20% to 35% by weight relative to the total weight of said essential oil, and an amount of chamazulene of less than or equal to 5%, preferably of less than or equal to 2% by weight, relative to the total weight of said essential oil.

By way of illustration, the cosmetic method according to the invention may be carried out by topical application, for example daily, of the essential oil of *Laserpitium siler* L. in accordance with the invention, which may for example be formulated in the form of creams, gels, serums, lotions, emulsions, milks for removing makeup or after-sun compositions.

The method according to the invention may comprise a single application.

According to another embodiment, the application is repeated, for example 2 to 3 times per day for one day or more, and generally for an extended period of at least 4 weeks, or even 4 to 15 weeks, with, where appropriate, one or more periods of stoppage.

Furthermore, treatment combinations with, optionally, oral or topical forms may be envisioned, in order to supplement or reinforce the activity of the essential oil of *Laserpitium siler* L. as defined by the invention.

Thus, a topical treatment with a composition containing an essential oil of *Laserpitium siler* L in accordance with the invention, combined with an oral or topical composition optionally containing another essential oil, could be imagined.

The ingredients are mixed, before being formed, in the order and under conditions that may readily be determined by a person skilled in the art.

According to one particular embodiment of the invention, other agents intended to enhance the appearance and/or texture of the skin could also be added to a composition that is suitable for the invention.

Throughout the description, including the claims, the expression "comprising a" should be understood as being synonymous with "comprising at least one", unless otherwise specified.

The expressions "between . . . and . . . " and "ranging from . . . to . . . " should be understood as meaning limits included, unless otherwise specified.

The examples and figures which follow are presented by way of illustration and without implied limitation of the invention. The compounds are, as the case may be, mentioned as chemical names or as CTFA (International Cosmetic Ingredient Dictionary and Handbook) names.

EXAMPLES

Example 1

Obtaining an Essential Oil According to the Invention 0.3 kg of seed-bearing umbels of freshly harvested fruits of *Laserpitium siler* L. are "fresh"-distilled without pretreatment.

This distillation is performed for 180 minutes according to the steam distillation (or hydrodistillation) technique in a 4-liter Clevenger type apparatus, i.e. of the same principle as that detailed in the European Pharmacopoeia (Ph. Eur. 4th Ed 2.8.12).

8 grams of an essential oil according to the invention are thus obtained.

The chemical analysis of the composition of the essential oil thus obtained is carried out by gas chromatography (GC) analysis.

The results indicate that an essential oil of *Laserpitium siler* L. in accordance with the invention comprises, as main compounds, limonene (68.95%), perillaldehyde (23.79%) and chamazulene (1.49%).

Example 2

Evaluation of the Effect of the Essential Oil of *Laserpitium Siler* L. According to Example 1 on NHDF Dermal Fibroblasts Material and Methods The study consists in evaluating, on NHDF (Normal Human Dermal Fibroblasts) dermal fibroblasts, the effects of the essential oil of *Laserpitium Siler* L. of example 1, at two concentrations, over the following parameters:
- the synthesis of type I procollagen by ELISA (CICP, Cross-linked C-telopeptides of Type I collagen) after 72 h of contact, and
- the abundance of MMP-1 secreted in the culture medium after 72 h of contact.

Methodology
Cell Culture

The study was carried out on NHDF human dermal fibroblasts (ATCC, CRL-2522, origin: foreskin) cultured in monolayer in a medium of DMEM (Invitrogen, 31885-049) and antibiotics (penicillin/streptomycin, Invitrogen, 15140-122), and cultured in serum-free medium for studies on type I collagen and on MMP-1.

The cells were maintained in a moist atmosphere at 37° C. containing 5% of $CO_2$.

| Products | Type | Supplier | Reference |
|---|---|---|---|
| Fibroblasts (NHDFs) | Cells | ATCC | CRL-2522 |
| DMEM | Culture medium | Invitrogen | 31885-049 |
| Penicillin/Streptomycin | Reagent | Invitrogen | 157140-122 |

Application of the Active Agents and of the Elements

The fibroblasts were seeded in 24-well plates, 24 h before the treatment with the test and reference elements.

For the measurement of the synthesis/secretion of type I procollagen and for the quantification of MMP-1, the test elements and also the reference elements (TGF-β1 (Transforming Growth Factor-β1) for MMP-1 and vitamin C for CICP) were applied for 72 h in the absence of serum.

The control fibroblasts were brought into contact with PBS (Phosphate Buffered Saline, Gibco, ref. 10010-015) for 30 min.

Quantification of the Synthesis/Secretion of Type I Procollagen

The supernatants of the cultures were harvested after 72 h of treatment with the active agents and the reference element (in this case, vitamin C at 1000 μM). These were frozen at −20° C. until the day of the analysis.

The measurement of the synthesis/secretion of type I procollagen was carried out with a specific kit (MicroVue CICP EIA Kit, Quidel, distributor: TECOmedical), according to the instructions given by the supplier.

The reference of the kit used is repeated in the table below:

| Products | Type | Supplier | Reference |
|---|---|---|---|
| Micro Vue CICP EIA Kit | Kit | Quidel | 8003 |

Quantification of MMP-1

As for CICP, the supernatants were harvested after 72 h of treatment with the active agents and the reference element, namely TGF-β1 at 2.5 ng/ml.

The quantification of MMP-1 was carried out with a specific kit (Human pro-MMP-1 Quantikine ELISA, R&D System), according to the instructions given by the supplier.

The reference of the kit used is repeated in the table below:

| Products | Type | Supplier | Reference |
|---|---|---|---|
| Human pro-MMP-1 Quantikine ELISA Kit | Kit | R&D System | DMP100 |

Results
Control without treatment=100%

| Treatment | Concentrations | Study of protein abundance CICP | MMP-1 |
|---|---|---|---|
| Vitamin C | 100 μM | 160%*** | / |
| TGF-β1 | 2.5 ng/ml | / | 47%*** |
| Essential oil of *Laserpitium Siler* L. | $2 \times 10^{-4}$% | 91% | 45%* |
|  | $2 \times 10^{-3}$% | 108%* | 93% |

According to the Student's test, which is a significance test, the value p is the following:
*: 0.01 to 0.05, significant
**: 0.001 to 0.01, very significant
***: <0.001, extremely significant The essential oil of *Laserpitium Siler* L. resulted in a significant decrease of 55% in the concentration of MMP-1 thus making it possible to protect the fibers of collagen, essential element of the dermis.

A significant slight stimulation of the synthesis of Pro-Coll1 makes it possible to supplement this activity and thus to reinforce the collagen fibers.

It is observed that said essential oil according to the invention makes it possible to decrease the concentration of MMP-1 while stimulating the synthesis of Pro-Coll1.

Thus, the essential oil of *Laserpitium Siler* L. stimulates the synthesis of collagen I via the stimulation of Pro-Coll1 while inhibiting the action of enzymes, namely the collagenase MMP 1.

Example 3

Effect of the Essential Oil of *Laserpitium Siler* L. According to Example 1 on the Synthesis of Collagen IV The purpose of this study was to evaluate the effects of the essential oil of *Laserpitium Siler* L. according to example 1 on the dermo-epidermal junction marker (Coll. IV) modulated during aging by immunohistochemistry techniques.
Protocol:
Culture medium: Keratinocyte-SFM supplemented with:
 Epidermal Growth Factor (EGF) 0.25 ng/ml
 Pituitary extract (PE) 25 μg/ml
 Gentamicin 25 μg/ml
Test medium: Keratinocyte-SFM supplemented with:
 Gentamicin 25 μg/ml
Normal human keratinocytes (NHEK—Ref: K341) were seeded and cultured in a culture medium (Keratinocyte-SFM for 24 hours). The culture medium was replaced by the test medium containing, or not containing (control), the test compounds or reference compounds (TGF-β at 10 ng/ml), then the cells were incubated for 72 hours at 37° C., 5% $CO_2$.

After incubation, the culture medium was removed and the cells were rinsed, fixed and permeabilized.

The cells were then labeled with the primary antibody targeted against the protein of interest (Collagen IV). This primary antibody was then revealed by a secondary antibody coupled to a fluorochrome (GAM-Alexa 488).
Results:
Effects of the compounds on the production of collagen IV by human keratinocytes.

The relative quantification was carried out by image analysis after in situ immuno labeling.

The image acquisition was carried out with a high-resolution imaging system: INCell Analyser™ 1000.

The essential oil of *Laserpitium Siler* L. induced the expression of collagen IV by normal human keratinocytes.

At 0.003% of essential oil, the expression of this marker of skin aging was increased by 45% (p between 0.01 and 0.05) compared to the untreated control.

The positive control TGF-β induced an increase of 594% compared to the control, validating the test.

Example 4

Evaluation of the Antioxidant Properties of the Essential Oil of *Laserpitium siler* L. According to Example 1

Material and Methods
a) Study of Squalene Peroxidation
Protocol

The principle of the test used is to determine, via the assaying of the squalene and of its photo-oxidation product, the efficacy of an active agent against this form of photo-peroxidation.

The test takes advantage of squalene in the presence of a photosensitizer, hematoporphyrin. Under the action of UVA radiation, the hematoporphyrin passes to an excited state. Via successive reaction, singlet oxygen ($^1O_2$) is generated. This highly reactive form of oxygen degrades the squalene by oxidation of the double bonds then rupture of these bonds and formation of degradation products, squalene peroxides.

Within the context of the test, the exposure of the squalene combined with the hematoporphyrin is carried out in the presence of various concentrations of essential oil of *Laserpitium siler* L. obtained according to example 1.
The reaction medium is ethanol.
The mixture (squalene/hematoporphyrin (80/20 v:v)+essential oil) is exposed over 45 min to UVA radiation (5 joules UVA/cm$^2$).
The assaying of the squalene and of the squalene peroxides is carried out by HPLC/UV.
Product Reference:
Squalene [Sigma S-3626].
Hematoporphyrin Free Base (approx. 70%) [Sigma—ref H-7253]
Result: Anti-$O_2$ Activity

| Raw materials | Concentration of essential oil of Laser Siler according to example 1 in ethanol | Activity (% inhibition) | Comments |
|---|---|---|---|
| ESSENTIAL OIL OF LASER SILER according to example 1 | 486.5 ppm<br>1459.5 ppm<br>4865.0 ppm | 12.6%<br>24.3%<br>48.9% | IC25 = 1550 ppm<br>IC50 = 5000 ppm |

The higher the concentration of essential oil of *Laserpitium siler* L. in the reaction medium, the less peroxidation of squalene there is.

b) Antioxidant Properties with Respect to Keratinocytes:
Protocol

HaCaT keratinocytes are brought into contact, within a culture medium, with the essential oil of Laser Siler according to example 1 for 24 hours at 37° C., 5% $CO_2$.

This culture medium is subjected to an oxidative stress under UVA radiation.

The keratinocytes, pretreated by the essential oil tested, are rinsed then incubated in the presence of the DHR123 probe in darkness for 30 min.

Measurement of the Fluorescence

The fluorescence of DCF is evaluated immediately after the exposure to UVA radiation, by spectrofluorimetry (excitation: 480 nm; emission: 530 nm).
Results:

The essential oil of *Laserpitium siler* L. limits the photooxidation of the cells by 50% at 0.1 g/l.

Conclusion

The essential oil of *Laserpitium siler* L. according to the invention has an antioxidant activity.

Example 5

Compositions

FACE CREAM in the Form of an Oil-in-Water (O/W) Emulsion

| Ingredients | Percentage by weight relative to the total weight of the composition (%) |
|---|---|
| Xanthan gum | 0.3 |
| MIXTURE OF PLANT ORIGIN OF LECITHIN, FATTY ACIDS AND FATTY ALCOHOLS BIOPHILIC H from LUCAS MEYER COSMETICS (UNIPEX) | 5 |
| ESSENTIAL OIL OF *LASERPITIUM SILER* L. obtained according to example 1 | 0.5 |
| SUNFLOWER OIL | 20 |
| CITRIC ACID ESTER OF GLYCERYL STEARATE AXOL C62 PELLETS from EVONIK GOLDSCHMIDT | 2 |
| FRAGRANCE | 0.3 |
| WATER | QS for 100 |

Applied to the skin of the face, this cream makes it possible to prevent and/or treat the signs of skin aging as described in the present invention.

FACE CREAM in the Form of an Oil-in-Water (O/W) Emulsion

| Ingredients | Percentage by weight relative to the total weight of the composition (%) |
|---|---|
| GLYCEROL | 4 |
| Xanthan gum RHODICARE CFT from RHODIA | 0.3 |
| MIXTURE OF PLANT ORIGIN OF LECITHIN, FATTY ACIDS AND FATTY ALCOHOLS BIOPHILIC H from LUCAS MEYER COSMETICS (UNIPEX) | 5 |
| ESSENTIAL OIL OF *LASERPITIUM SILER* L. according to example 1 | 0.4 |
| SUNFLOWER OIL | 15 |
| JOJOBA OIL | 5 |
| CITRIC ACID ESTER OF GLYCERYL STEARATE AXOL C62 PELLETS from EVONIK GOLDSCHMIDT | 2 |
| BENZYL ALCOHOL | 0.5 |

-continued

| Ingredients | Percentage by weight relative to the total weight of the composition (%) |
|---|---|
| FRAGRANCE | 0.3 |
| Phenoxyethanol Protectol PE from BASF | 0.6 |
| WATER | QS for 100 |

Applied to the skin of the face, this cream makes it possible to combat the skin disorders induced by an oxidative stress as defined in the present invention.

The invention claimed is:

1. A cosmetic method for treating signs of skin aging, signs of photoaging, skin disorders induced by an oxidative stress selected from the group consisting of at least one of a dull appearance of a subject's complexion, hyperpigmentation of the skin, a loss of quality of a subject's sebum, and a feeling of discomfort on a subject's scalp, in a subject in need thereof, the method comprising topically applying to the skin or scalp of said subject a composition comprising an effective amount of an essential oil of *Laserpitium siler* L., wherein the essential oil of *Laserpitium siler* L. comprises limonene in an amount ranging from 40% to 80% by weight relative to the total weight of said essential oil, perillaldehyde in an amount ranging from 15% to 40% by weight relative to the total weight of said essential oil, and chamazulene being present in a positive amount of up to 5% by weight relative to the total weight of the essential oil.

2. The method as claimed in claim 1, wherein said essential oil is obtained from leaves and/or umbels and/or seed-bearing umbels and/or seeds of the fruits of *Laserpitium siler* L.

3. The method as claimed in claim 2, wherein said essential oil is obtained from umbels of *Laserpitium siler* L.

4. The method as claimed in claim 2, wherein said essential oil is obtained from leaves of *Laserpitium siler* L.

5. The cosmetic treatment method as claimed in claim 1, wherein said essential oil is used at a content ranging from 0.0001% to 10% by weight, relative to the total weight of the composition comprising the essential oil of *Laserpitium siler* L.

6. The method as claimed in claim 2, wherein said essential oil is obtained from seed-bearing umbels of *Laserpitium siler* L.

7. The method as claimed in claim 1, wherein said essential oil of *Laserpitium siler* L. comprises limonene in an amount ranging from 50% to 70% by weight relative to the total weight of said essential oil, perillaldehyde in an amount ranging from 20% to 35% by weight relative to the total weight of said essential oil, and chamazulene in an amount of up to 2% by weight relative to the total weight of said essential oil.

* * * * *